(12) United States Patent
Walba

(10) Patent No.: US 9,187,500 B2
(45) Date of Patent: Nov. 17, 2015

(54) LIQUID CRYSTAL DEVICES FOR INFORMATION DISPLAY AND PHOTONICS APPLICATIONS

(75) Inventor: David M Walba, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 34 days.

(21) Appl. No.: 13/548,999

(22) Filed: Jul. 13, 2012

(65) Prior Publication Data

US 2013/0016295 A1 Jan. 17, 2013

Related U.S. Application Data

(60) Provisional application No. 61/507,912, filed on Jul. 14, 2011.

(51) Int. Cl.
| | |
|---|---|
| C09K 19/20 | (2006.01) |
| C09K 19/40 | (2006.01) |
| C07F 7/08 | (2006.01) |
| G02F 1/141 | (2006.01) |
| C09K 19/02 | (2006.01) |

(52) U.S. Cl.
CPC ........... C07F 7/0818 (2013.01); C09K 19/0225 (2013.01); C09K 19/406 (2013.01); G02F 1/1416 (2013.01); G02F 1/1418 (2013.01); C09K 19/2007 (2013.01)

(58) Field of Classification Search
CPC .......... C09K 19/0241; C09K 19/2007; C09K 19/406; C09K 19/0225; G02F 1/1365; C07F 7/0818
USPC ............ 252/299.01, 299.67; 349/41; 556/416
See application file for complete search history.

(56) References Cited

U.S. PATENT DOCUMENTS

| | | | |
|---|---|---|---|
| 4,813,767 A | 3/1989 | Clark et al. | |
| 7,463,233 B2 | 12/2008 | Kim | |
| 2010/0014029 A1* | 1/2010 | Nakamura et al. ............. | 349/74 |

OTHER PUBLICATIONS

CAPLUS 2010:962985.*
Korblova et al., "Design and Synthesis of an Achiral Ferroelectric Smectic Liquid Crystal", Liquid Crystals XV, Proc. of SPIE vol. 8114, 81140X, 2011.*
Clark et al., "Submicrosecond bistable electro-optical switching in liquid crystals" Appl. Phys. Lett., vol. 36 No. 11, Jun. 1980, pp. 889-901.
Walba, D. M., "Chiral sMa* material for display applications?" Journal of the SID, vol. 15(8), (2007), pp. 585-588.

* cited by examiner

*Primary Examiner* — Shean C Wu
(74) *Attorney, Agent, or Firm* — Lathrop & Gage LLP

(57) ABSTRACT

A novel approach for generating FLC electro-optics with gray-scale resolution includes using FLC material that is: (i.) capable of electrostatic V-shape switching, (ii.) capable of optical latching, and (iii.) not requiring DC balance.

11 Claims, 18 Drawing Sheets

1: $R_1 =$ $OC_9H_{19}$; $R_2 = C\equiv N$
   X-129.5°C-SmAP$_A$-138°C-SmA-140.2°C-Iso 2: $R_1 =$ O-(CH$_2$)$_{11}$Si(CH$_3$)$_2$Si(CH$_3$)$_2$Si(CH$_3$)$_3$; $R_2 = C\equiv N$
   X-110°C-SmAP$_F$-137°C-SmA-155°C-Iso 3: $R_5 = R_4 = OC_9H_{19}$; $R_5 = X = H$
   X-72°C-B3-140°C-SmC$_S$P$_A$-158°C-Iso 4: $R_3 = R_4 = OC_8H_{17}$; $R_5 = CN$; $X = F$
   X-73°C-SmAP$_A$- T$_1$=145°C -SmA-180°C-Iso 5: $R_3 = OC_9H_{19}$; $R_4 = $ [structure: $-C(O)O-C_6H_{13}$]; $R_5 = X = H$
   B4-90°C-SmCP (B7)-139°C-Iso 6: $R_3 = R_4 = $ [branched alkoxy structure]; $R_5 = X = H$
   B3*-138°C-SmY*-146°C-SmC$_A$P$_F$*-167°C-Iso

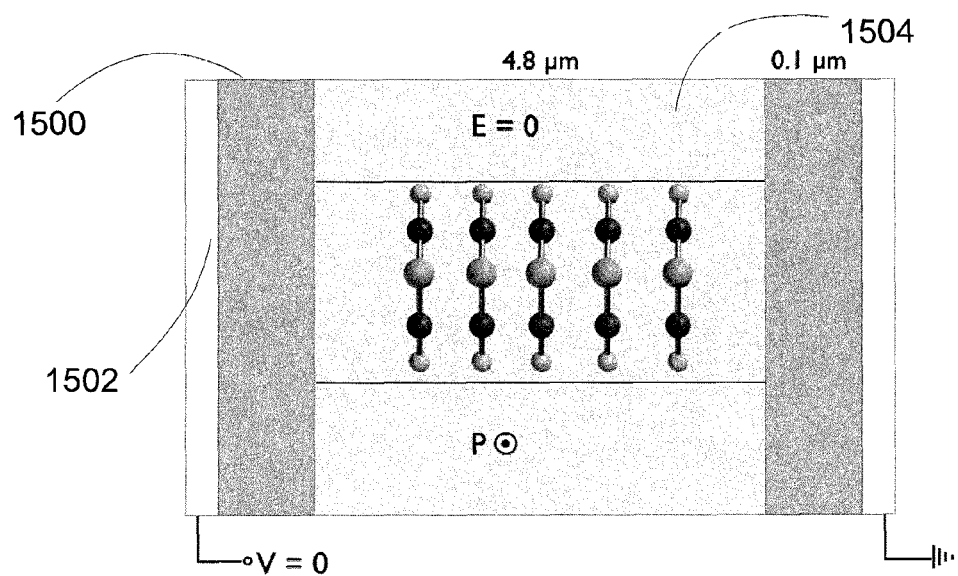
FIG. 15A
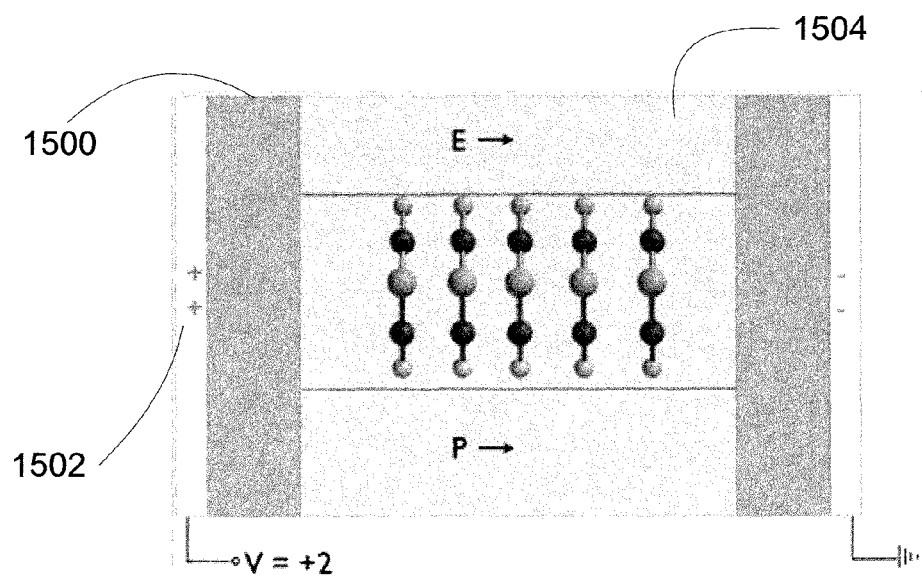

Experimental data for "T3"

LIQUID CRYSTAL DEVICES FOR INFORMATION DISPLAY AND PHOTONICS APPLICATIONS

RELATED APPLICATIONS

This application claims benefit of priority to U.S. Provisional Patent Application 61/507,912 filed Jul. 14, 2011, which is hereby incorporated by reference to the same extent as though fully replicated herein.

GOVERNMENT RIGHTS

This invention was made with government support under grant number DMR 0820579 awarded by the National Science Foundation. The government has certain rights in the invention.

BACKGROUND

The disclosure relates to ferroelectric liquid crystal (FLC) material. More particularly, this disclosure involves approaches for generating FLC electro-optics with gray-scale resolution using FLC material that is: (i.) capable of electrostatic V-shape switching, (ii.) capable of optical latching, and (iii.) not requiring DC balance.

DESCRIPTION OF THE RELATED ART

Liquid crystals (LC) are materials with the fluidity of a liquid and the anisotrophy of crystals. In particular, ferroelectric liquid crystal (FLC) materials, involving spontaneous electric polarization of a material that is reversible by applying an external electric field, have applications across a variety of fields. For example, FLCs are successfully commercialized as liquid crystal on silicon (LCOS) microdisplays for camera viewfinders and pico-projectors. A potential large market exists for FLC materials capable of rapid performance to replace nematic liquid crystals in LCDs. However, two technical caveats inhibit broad utilization of FLCs in such markets, including the inability for known FLC devices to provide gray-scale and the liklihood for a "DC balance" problem.

One approach for creating a perceived gray-scale and full color image, such as in the commercial 3M pico projection (e.g., Mpro 120, Mpro 150), utilizes time-sequential writing with an FLC LCOS microdisplay illuminated by separate red, green, and blue LEDs. However, in order to maintain a net DC balance on the LC, image elements are "balanced" by writing the negative of the image elements with the lights turned off, thereby halving the brightness achievable with a given light source. Moreover, for many applications, including information display, true gray-scale would be advantageous. For example, a FLC-based device capable of true gray-scale could be a "drop-in" replacement for nematic LCs in LCD television, but performing much faster.

However, neither the "bistable" switching mode of current FLC LCOS devices, nor known gray-scale modes of current nematic LC devices, provide optical latching. In devices capable of optical latching, once an image is written, it may be held substantially without dissipation of power. For example, the e-ink technology used in the Amazon Kindle is capable of this, but cannot provide gray levels in the current devices, and e-ink is not fast enough for motion video display.

U.S. Pat. No. 7,463,233 describes generally the field of prior art ferroelectric LCD's.

SUMMARY

The presently disclosed instrumentalities advance the art and overcome the problems outlined above by providing an approach to generate FLC electro-optics with gray-scale resolution using FLC material that is: (i.) capable of electrostatic V-shape switching, (ii.) capable of optical latching, and (iii.) not requiring DC balance.

The present disclosure provides a method for producing liquid crystal electro-optics that comprises providing ferroelectric liquid crystal (FLC) material between two electrodes, permitting the FLC material to assemble into a plurality of layers, applying voltage to the electrodes to facilitate V-switching of the FLC material, maintaining constant voltage on the electrodes to facilitate optical latching, and eliminating the requirement for DC balance. In nonlimiting examples, this approach may occur using calamitic molecules or bent-core molecules. In one embodiment, this approach occurs using a polar SmAP$_F$ FLC material.

In one embodiment, a liquid crystal electro-optic device contains an interior formed of a ferroelectric liquid crystal (FLC) material having mesogens of a formula:

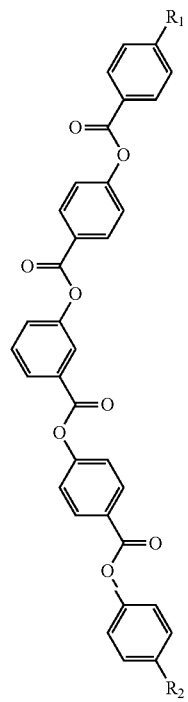

wherein R$_1$ is

O—R$_{1a}$—R$_{1b}$ where

R$_{1a}$ is (CH$_2$)$_n$ with n being an integer from 1 to 15. Odd integers are preferred as some even integers may not render a ferroelectric phase, and (CH$_2$)$_{11}$ is particularly preferred.

R$_{1b}$ is (Si(R$_{1c}$))$_q$ where R$_{1c}$ is alkyl, methyl, ethyl and combinations thereof, and q is an integer from one to four. Preferred forms of R$_{1b}$ include Si(CH$_3$)$_2$Si(CH$_3$)$_2$ Si(CH$_3$)$_2$; Si(CH$_3$)$_2$Si(CH$_3$), Si(CH$_3$); Si(C$_2$H$_5$)$_2$; Si(C$_2$H$_5$)$_2$Si(C$_2$H$_5$)$_2$; Si(C$_2$H$_5$)$_2$ Si(C$_2$H$_5$)$_2$; and Si(C$_2$H$_5$)$_2$, with Si(CH$_3$)$_2$Si(CH$_3$)$_2$Si(CH$_3$)$_2$ being particularly preferred.

R₂ may be:

C≡N (cyano);

NO₂ (nitro);

O—CF₃ (trifluoromethoxy); or

C₄F₉O—C₂F₄O—CF₂CH₂O, with C≡N being particularly preferred.

A pair of conductive electrodes are operably positioned with respect to the FLC material for altering a polarization angle inherent to the FLC material in response to an applied field. A change in the polarization angle switches the FLC material from a first optical state to a second optical state. Control circuitry is operable to apply a plurality of voltages that switch the FLC material and thereafter maintain the optical state by maintaining a voltage across the FLC material. In this manner, the control circuitry is operable to change the optical state from an opaque state to an optically transmissive state, as well as one or more grey scale state therebetween.

BRIEF DESCRIPTION OF THE FIGURES

FIGS. 15A, 15B, 15C, 15D, and 15E show optical latching in a FLC-based device containing a conducting material and liquid crystal material.

DETAILED DESCRIPTION

The presently disclosed instrumentalities advance the art by providing an approach to generate FLC electro-optics, such as FLC-based devices, with gray-scale resolution using FLC material that is: (i.) capable of electrostatic V-shape switching, (ii.) capable of optical latching, and (iii.) not requiring DC balance. In the current disclosure, the requirement for DC balance is eliminated in electrostatic V-shape switching since no electric field exists within the liquid crystal layer of a device, thereby avoiding accumulation of ions at the device surface. The current disclosure provides optical latching since achievement of a gray-scale state from V-shape switching eliminates the requirement for power dissipation until modifying a gray-scale state. In nonlimiting examples, said approach may occur using calamitic molecules or bent-core molecules. These materials may, for example, be used in place of liquid crystals that are disclosed for use in bookshelf SSFLC devices of the type shown and described in Clark et al., "Submicrosecond bistable electro-optical switching in liquid crystals," Appl. Phys. Lett., Vol. 36 No. 11, June 1980; and as shown in U.S. Pat. No. 4,813,767 issued to Clark et al., both of which are incorporated by reference to the same extent as though fully replicated herein.

As used herein, a smectic phase, or a smectic layer, refers to a particular LC phase having translational order and orientational order. As used herein, "translation order" refers to a group of molecules with spatial arrangement, whereas "orientational order" refers to a group of molecules with alignment in a similar direction along a plane, termed a director. In particular, smectic-$AP_F$ ($SmAP_F$) phases may have polar ordering and three-dimensional ferroelectric ordering of layer polarization. A plurality of smectic layers, such as $SmAP_F$ layers, may be assembled to generate a supramolecular arrangement containing a system of smectic layer interfaces.

Figure 1A:
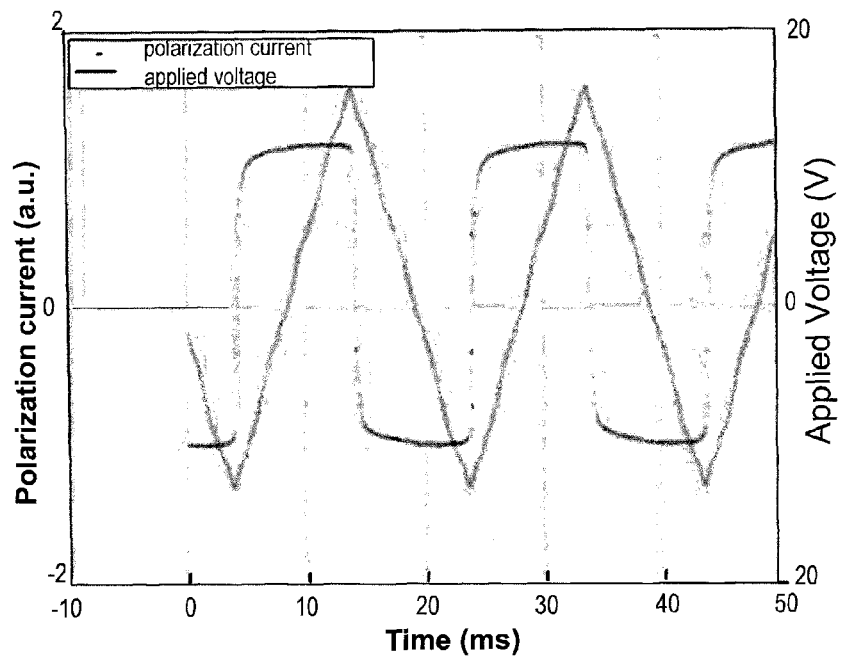
FIGS. 1A and 1B show optical latching in electrostatic V-shaped switching.
Figure 1B:
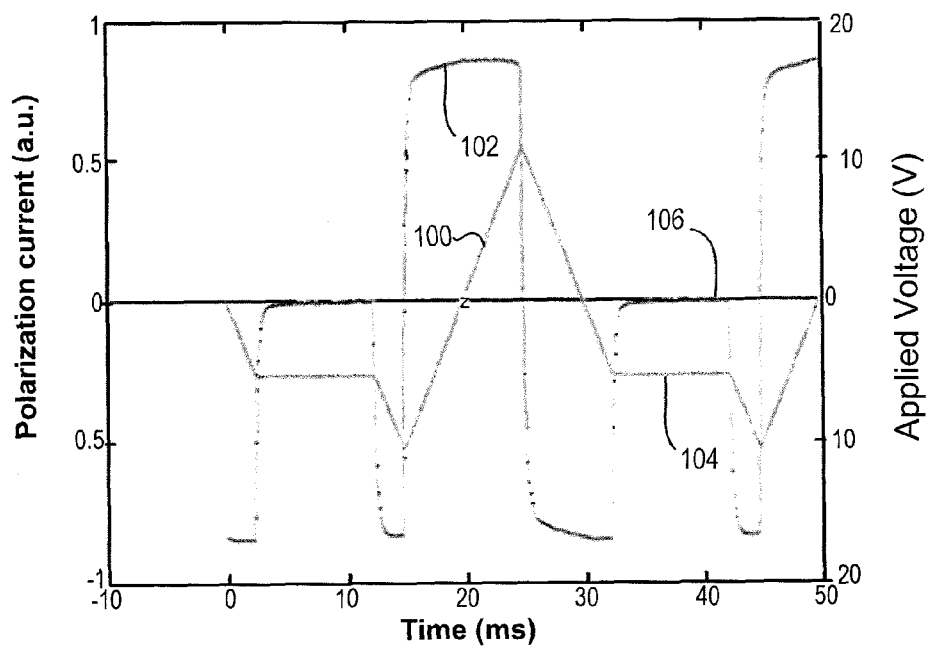

FIGS. 1A and 1B show the achievement of optical latching in electrostatic V-shaped switching using smectic phase materials according to the present disclosure. As shown in FIG. 1B, when applied voltage is constantly changing 100, the current is approximately constant 102. Moreover, when the applied voltage is constantly changing, the orientational order of the molecules is also changing. Upon maintaining a constant applied voltage 104, the current drops to zero 106, as shown in FIG. 1B. When this constant applied voltage is used, the orientation order of the molecules is maintained FIG. 1 illustrates that the current disclosed instrumentalities provide optical latching wherein a written electro-optic image may be maintained without dissipation of power. In one embodiment, optical latching is achieved using a polar $SmAP_F$ FLC material.

Figure 2A:
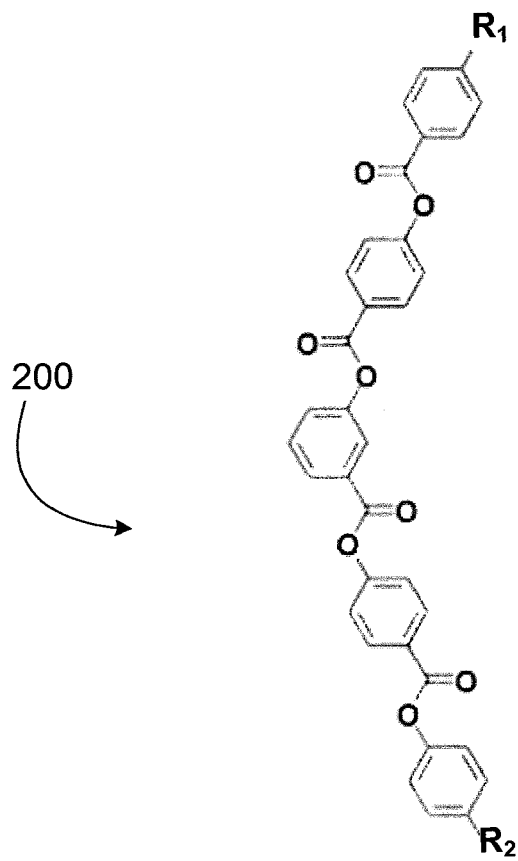
FIG. 2A shows a bent-core mesogen structure that is capable of forming a smectic ferroelectric phase by comparison to the prior molecules of FIG. 2B.

Molecules according to the presently disclosed instrumentalities generate $SmAP_F$ material with anticlinic smectic layer interfaces using a bent-core molecular design. For example, FIG. 2A shows a bent-core molecule structure 200 that may contain different molecular constituents to generate different bent-core molecular structures. In nonlimiting examples disclosed below, a system of smectic anticlinic layer interfaces is achieved by using bent-core molecules containing siloxane or poly-fluorinated hydrocarbon constituents.

With reference to FIG. 2A, $R_1$ may be:
O—$R_{1a}$—$R_{1b}$ wherein
$R_{1a}$ is $(CH_2)_n$ with n being an integer from 1 to 15. Odd integers are preferred as some even integers may not render a ferroelectric phase, and $(CH_2)_{11}$ is particularly preferred.
$R_{1b}$ is $(Si(R_{1c}))_q$ where $R_{1c}$ is alkyl, methyl, ethyl and combinations thereof, and q is an integer from one to four. Preferred forms of $R_{1b}$ include $Si(CH_3)_2Si(CH_3)_2$; $Si(CH_3)_2$; $Si(CH_3)_2Si(CH_3)$; $Si(CH_3)$; $Si(C_2H_5)_2$, $Si(C_2H_5)_2Si(C_2H_5)_2$; $Si(C_2H_5)_2Si(C_2H_5)_2$; and $Si(C_2H_5)_2$, with $Si(CH_3)_2Si(CH_3)_2Si(CH_3)_2$ being particularly preferred.
$R_2$ may be:
C≡N (cyano);
$NO_2$ (nitro);
O—$CF_3$ (trifluoromethoxy); or
$C_4F_9O$—$C_2F_4O$—$CF_2CH_2O$, with C≡N being particularly preferred.

Figure 2B:
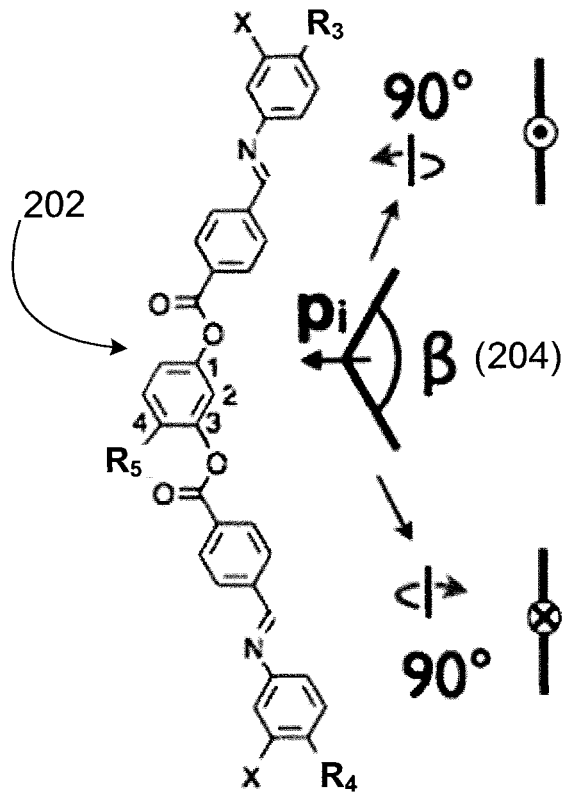

By way of example, where $R_1$ is O—$C_9H_{19}$ and $R_2$ is C≡N (Compound 1), the molecules form $SmAP_A$ phase at 129.5° C. to 138° C. and enter SmA phase at 140.2° C. These molecules are antiferroelectric and do not perform as ferroelectrics in response to applied field as described below. On the other hand, when R1 is O—$(CH_2)_{11}$—$Si(CH_3)_2Si(CH_3)_2Si(CH_3)_2$ and R2 is C≡N (Compound 2), the molecules form $SmAP_F$ (ferroelectric) phase at 110° C. to 137° C. and enter SmA phase at 155° C. These molecules demonstrate ferroelectric behavior in response to applied field as described below. Without being bound by theory, it is believed that the bent-core molecular structure assists with tilt and polar ordering. In general, for smectic LC phases comprising bent-core molecules with tails, the fluid core and tail sublayers are nanosegregated. The biaxial shape, molecular bend, and long polarizable aromatic cores (e.g., 5 aromatic rings) of the bent-core molecules reduce out-of-layer fluctuations owing to layer stratification and stabilization of similar molecular components of the bent-core mesogen within a layer, such associating like-molecular subcomponents of the bent-core molecules at the same level within a layer. For a layer of untilted bent-core molecules, the neighboring molecules are spatially adjacent resulting in steric interactions and/or electrostatic repulsion of neighboring molecules and competition for free volume between neighboring molecules. Conversely, a coherent tilt of the bent-core molecules provides a means to obtain lower entropic and enthalpic free energy interactions with complementary molecular regions of neighboring bent-core mesogens. If interactions between complementary molecular neighbors are weakened, as in the case of short rod-shaped mesogens with strong out-of-layer fluctuations, then untilted layers likely result. For example, featureless bent-rods form untilted phases in simulations. For bent-core molecules, steric shape promotes polar ordering, owing to the efficient filling space and lower overall entropy if the bent-core molecules bend in the same direction. The bent-core molecules undergo self-assembly into SmCP phases To illustrate a comparison with other bent-core molecules of the prior art. FIG. 2B shows bent-core structure, structure 202, which may be modified with different molecular constituents to generate different bent-core structures. For example, molecule 202 contains differing molecular constituents resulting in compounds 3, 4, 5 or 6. Of these, most are anti-ferroelectrics and only one of those shown, Compound 6, is capable of ferroelectric response and this occurs generally at a higher temperature than molecules according to FIG. 2A.

Bent-core structure 202 contains an opening angle-β 204. In one example, angle-β 204 is larger in Compound 4 owing to the CN substitution.

At $R_1$, the bent-core molecules of the present disclosure contain a flexible constituent, or tail, that stabilize fluidic smectic layers. In one embodiment, the bent-core molecule contains a single tail. In another embodiment, a silane-containing tail suppresses out-of-layer fluctuations to enable ferroelectric coupling between adjacent layers.

Figure 3:
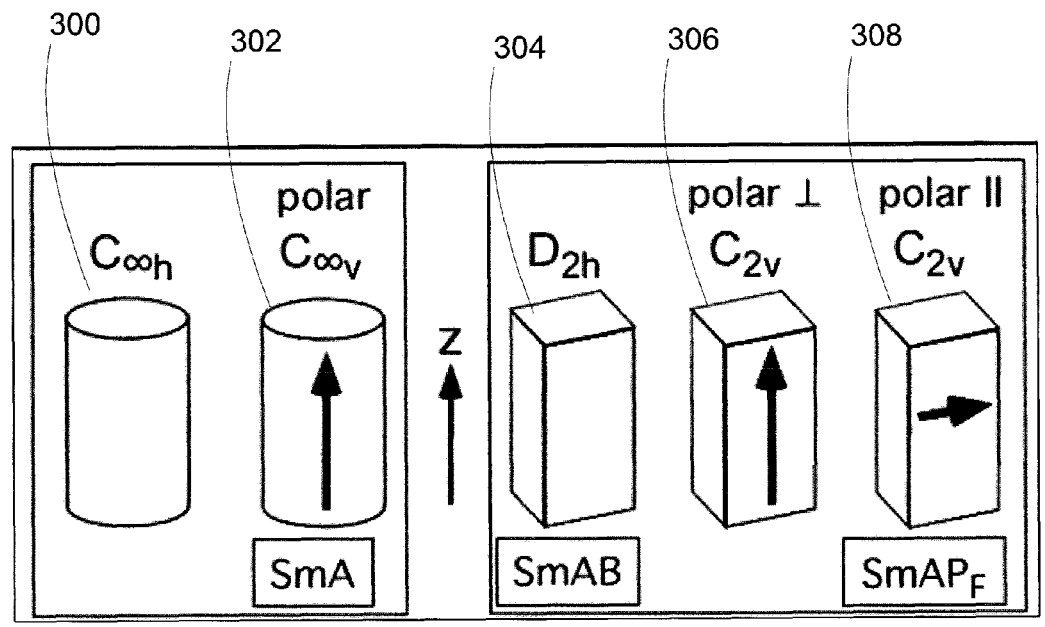
FIG. 3 shows various layers configurations of orthogonal achiral smectic phases.

The smectic phase materials described herein may be placed in different operable orientations as they orient themselves in layers relative to applied field. FIG. 3 shows various layer configurations of orthogonal achiral smectic phases. Uniaxial layer ($C_{\infty h}$) 300 has a SmA phase and may display high susceptibility for field-induced in-plane polar order. Uniaxial polar layer ($C_{\infty v}$) 302 has a smectic A phase. Nonpolar orthorhombic layer ($D_{2h}$) 304 has a biaxial SmAB phase. Polar orthorhombic layer ($C_{2v}$) has a SmAP phase that may be found with in-plane layer polarization and macroscopic antiferroelectric ordering of adjacent layers ($SmAP_A$). Polar orthorhombic layer ($C_{2v}$) 306 shows polarity perpendicular to the normal plane, whereas polar orthorhombic layer ($C_{2v}$) 308 shows polarity parallel to the normal plane.

Figure 4:
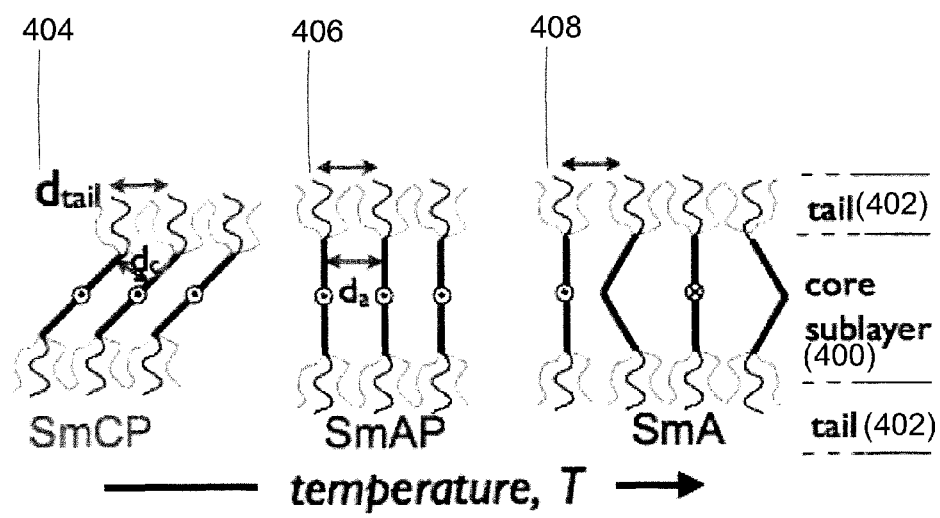
FIG. 4 shows smectic LC phases that include a core sublayer and a tail.

Temperature also affects materials performance. FIG. 4 shows various smectic LC phases that include a core sublayer 400 and a tail 402. FIG. 4 also shows that phase structures depend upon mesogen structure as a function of temperature, such as a reversible transition from SmCP phase 404 to a SmAP phase 406 and then a SmA phase 408, all depending on the increase or decrease of temperature.

Figure 5:
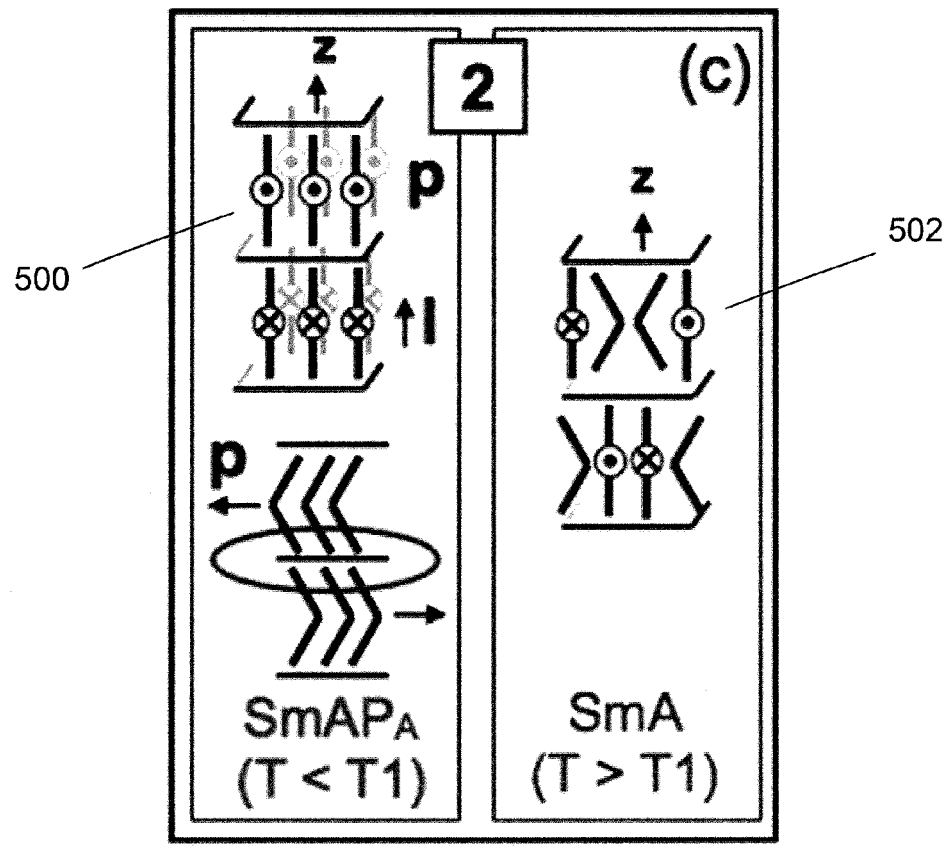
FIG. 5 shows the supermolecular structure of a $SmAP_A$ phase.

FIG. 5 shows the supermolecular structure of the antiferroelectric $SmAP_A$ phase 500 observed in Compound 4 (See FIG. 2), showing the average molecular long axis layer, l, parallel to the layer normal z, and the average molecular polar axis p, normal to z. The $SmAP_A$ phase 500 is stabilized by the synclinic ordering of the molecular tails at the layer interfaces, indicated in the ellipse. The SmA phase 502 appears in Compound 4 at higher temperature.

Figure 6:
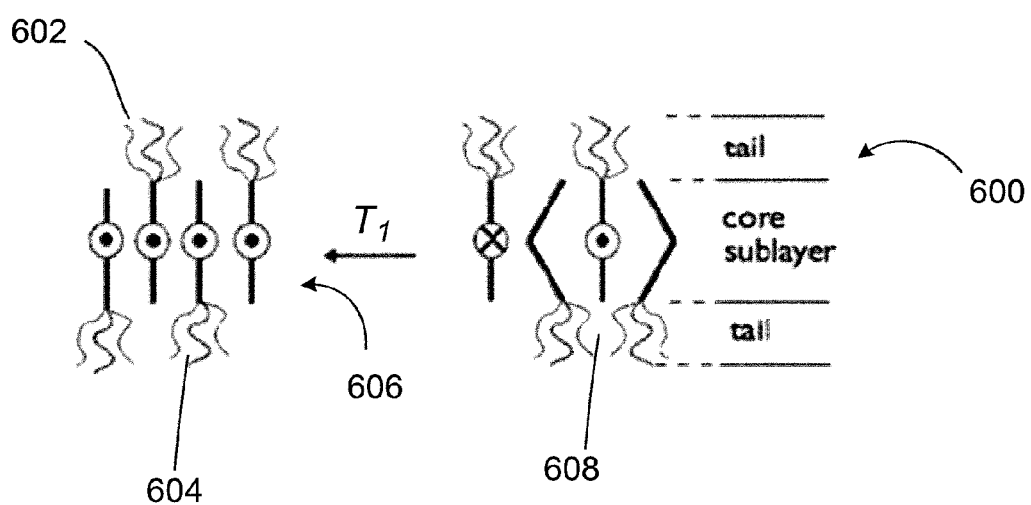
FIG. 6 shows a schematic of tail manipulation.

FIG. 6 shows a single layer 600 that may self-order to stack in a plurality of such layers. In these materials, strong dispersive attractions exist between cores with aromatic rings and which possess a strongly biaxial shape. This drives sideways tilt in the smectic phase. This problem may be redressed by tail manipulation, such as by reducing the number of tails 602, 604 within any mesogen from two tails to a single tail, creates additional space and promotes orthogonal phases for the layers. Without being bound by theory, tails in adjacent layers interdigiate and provide layer spacing larger than molecular length. At low temperature, steric interaction is enhanced between the layers and results in a SmAP phases 606, whereas at high temperature, steric interaction is reduced between the layers resulting in SmAP phase 608.

Properties of FLC materials, and the accompanying FLC devices, may depend upon transition temperatures the influence the Clark-Lagerwall effect. Some FLC electro-optic materials and accompanying FLC-based devices, with gray-scale resolution may occur utilizing materials with minimal temperature dependence. For example, device materials may include chiral SmA materials as described in Walba D. M., Journal of the SID, Vol. 15(8), (2007), which is incorporated herein by reference in its entirety.

The following examples set forth FLC electro-optics, such as FLC-based devices, with gray-scale resolution using FLC material. It is to be understood that these examples are provided by way of illustration and should not be unduly construed to limit the scope of what is disclosed herein.

EXAMPLE 1

Generation of $SmAP_F$ Phase Using a Tri-Carbosilane Modified Mesogen

Figure 14:
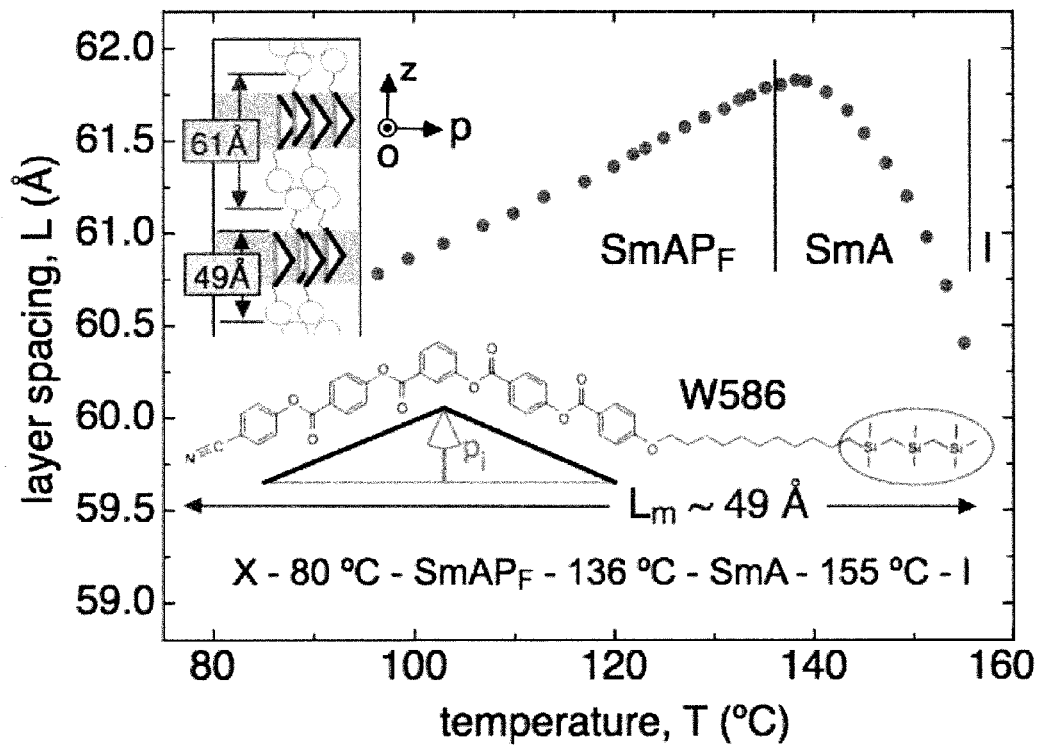
FIG. 14 shows birefringence of planar-aligned cells.

The following nonlimiting example teaches by way of illustration, not by limitation, generation of $SmAP_F$ phase using Compound 2 (See FIG. 2). X-ray, optical, and calorimetric studies of Compound 2 provide evidence for the SmAPF phase, showing the phase sequence: crystal (X)—80° C.—$SmAP_F$—136° C.—SmA—155° C.—isotropic (I) vs. temperature, T. In both the SmA and $SmAP_F$ phases, x-ray diffraction vs. T exhibited a resolution-limited first-order reflection due to the smectic layering in the small angle region, and diffuse scattering with a peak at a spacing D~4.6 Å, indicating smectic layering with liquid-like in-plane order. The layer spacing L~62 Å is much larger than the calculated extended (all trans) molecular length $L_m$~49 Å, (see FIG. 14), suggesting the interdigitated partial bilayer smectic structure proposed in FIG. 2 in both phases.

EXAMPLE 2

Optical Property Characterization of a Tri-Carbosilane Containing Mesogen

The following nonlimiting example teaches by way of illustration, not by limitation, optical property characterization of a tri-carbosilane modified mesogen, namely Compound (See FIG. 2). In particular, the optical textures of Compound 2 were studied using four distinct preparation methods: (1) homeotropic cells, (2) aligned planar cells, (3) freely suspended films, and (4) random polar cells.

Figure 7:
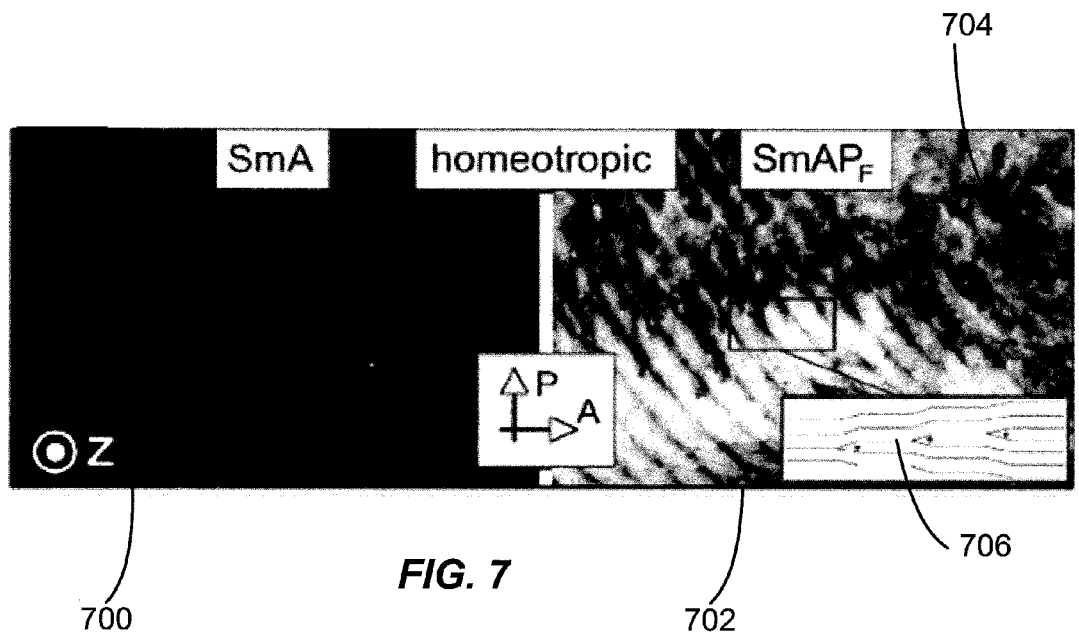
FIG. 7 shows an image of a SmA phase and a $SmA_F$ phase formed on glass plates.

Preparation of homeotropic cells, or homeotropic aligned samples, with Compound 2 occurred using clean glass plates. As used herein, homeotropic alignment refers to a state wherein rod-like mesogens, within a liquid crystal, align perpendicular to a substrate. In one embodiment, smectic layers are parallel to glass plate substrates. As shown in FIG. 7, Compound 2 yielded a SmA phase as identified by the excellent extinction between crossed polarizer and analyzer in the homeotropic texture, evidence for an optical uniaxis normal to the layers and plates. Since homeotropic alignment of the SmA phase is not optically anisotrophic, a dark field 700 was present. Upon cooling the sample, a $SmAP_F$ phase 702 was generated, as evidenced by the appearance of distinct Schlieren texture 704, or optical inhomogeneous texture, of in-layer birefringence as shown in FIG. 7.

Additionally, a quasi-periodic pattern of stripes 706 were present in the sample. Stripes 706 marked the termination of a single smectic layer accommodating spatial variation of the gap between glass plates. For example, the appearance of these stripes is analogous to that found in homeotropic samples of rod-like molecules as one passes through the SmA to SmC transition. Conoscopy of the hometropic samples with Compound 2 showed uniaxial orientation in the SmA phase and locally biaxial ordering with an optical axis normal to the layers and increasing in-plane birefringence Δn with decreasing temperature in the $SmAP_F$ phase.

Figure 8:
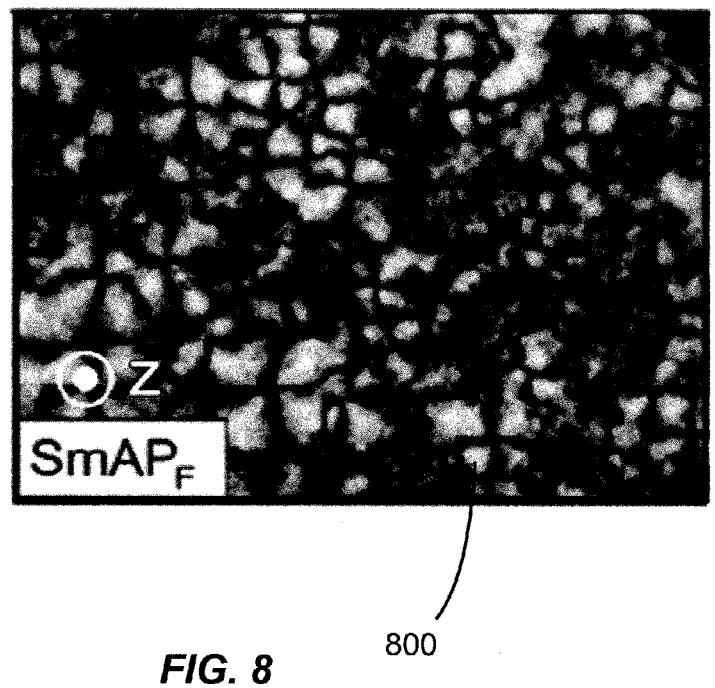
FIG. 8 shows Schlieren texture of a homeotropic aligned sample prepared containing a $SmAP_F$ phase.

FIG. 8 also shows Schlieren texture 800 of a homeotropic aligned sample prepared with Compound 2, here containing a $SmAP_F$ phase. The Schlieren texture 800 of FIG. 8 is characterized by smooth brush patterns indicative of slowly varying optical anisotropy and, therefore, in-layer orientational ordering of the molecular bow-planes. FIG. 8 also demonstrates polar ordered of the $SmAP_F$ phase by showing defects with four-brush patterns between crossed polarizer and analyzer, indicating a 2π reorientation of an optic axis about each defect core.

Figure 9:
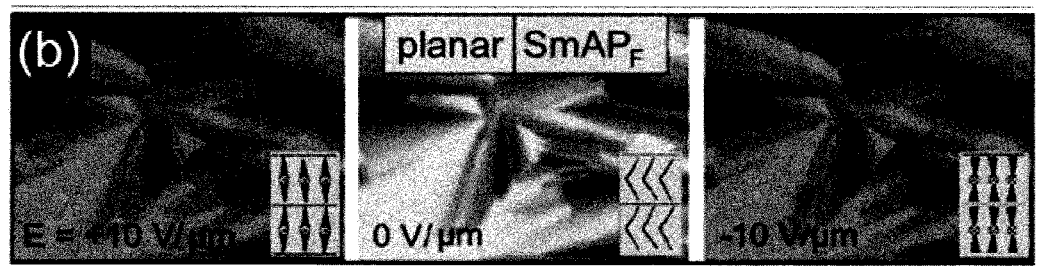
FIG. 9 shows images of nylon films on glass resulting in random planar focal conics with layers normal to the plates.

Preparation of random planar samples with Compound 2 occurred using clean glass plates. The random planar samples exhibited focal conic textures, which showed a strong increase of effective birefringence with applied electric field of either sign normal to the plates, but no accompanying SmC-like optic axis rotation about the applied field direction (FIG. 9).

Figure 10:
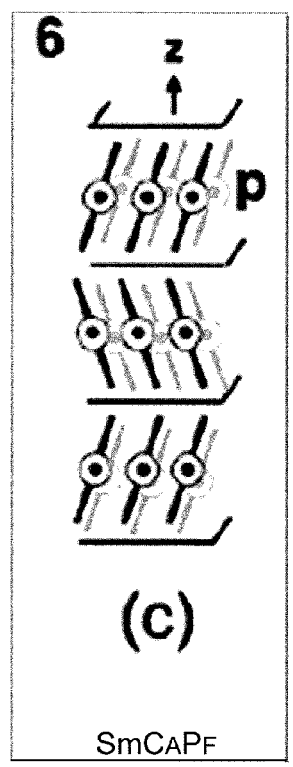
FIG. 10 shows a schematic of $SmC_AP_F$ phases.
Figure 11:
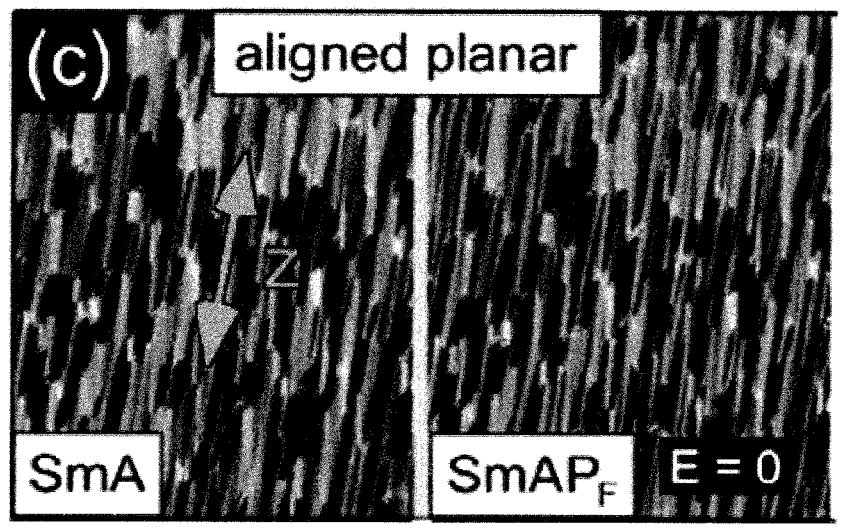
FIG. 11 shows images of Teflon rubbed films on glass resulting in uniform planar alignment of phases.

This observation and the homeotropic Schlieren texture indicates that one optical dielectric tensor principal axis (PA), is along the layer normal z and that the other two, p and o, are in the layer plane. Here $p(\Psi)=<p(\phi_i)>$ is the mean of the molecular vectors, where $p(\phi_i)$ gives the azimuthal orientation $\phi_i$ of the bow plane of molecule i in a layer, $\Psi=\arccos <\cos\phi_i>$ is the orientation of p, and o is mutually normal to z and to p. In this frame, the optical dielectric tensor ε is diagonal, with respective principal optical dielectric constants, $\epsilon_z=n_z^2$, $\epsilon_p=n_p^2$, and $\epsilon_o=n_o^2$ (see FIGS. 5 and 14). This orientation of the optical principal axes (PA) and the sign of birefringence in the planar geometry indicating that $\epsilon_z$ is the largest, provides direct evidence that this polar smectic phase has the mean molecular long axis normal to the layers, indicating the $SmAP_F$, or possibly, $SmC_AP_F$ (see FIG. 10). Remarkably, a well-aligned planar texture with z parallel to the glass plates and the rubbing direction was obtained for both the smectic A phases in the rubbed Teflon cells, as shown in FIG. 11, a rare case in which a smectic phase of bent-core mesogens has been successfully aligned by rubbing.

To probe the in-layer molecular orientation and the electric polarization fields in smectic liquid crystals phases of rod-like and bent-core molecules, freely suspended films (FSFs) are drawn in air with an integer number of smectic layers and further characterized using Depolarized Reflected Light Microscopy (DRLM) with oblique laser illumination. This approach is herein referred to as DRLM-film technique. As is typical for fluid smectics, FSFs are an integral number, N, of smectic layers thick. In one embodiment, N is in the range, 1<N<10.

The DRLM-film technique was used to probe the ground state structure of the observed smectic phase using Compound 2. Films of uniform thickness with N in the range, 1<N<10, as well as films with layer steps, were prepared by drawing them over a 5 mm diameter hole in a glass cover slip. Film thickness was determined by laser reflectivity.

Figure 12:
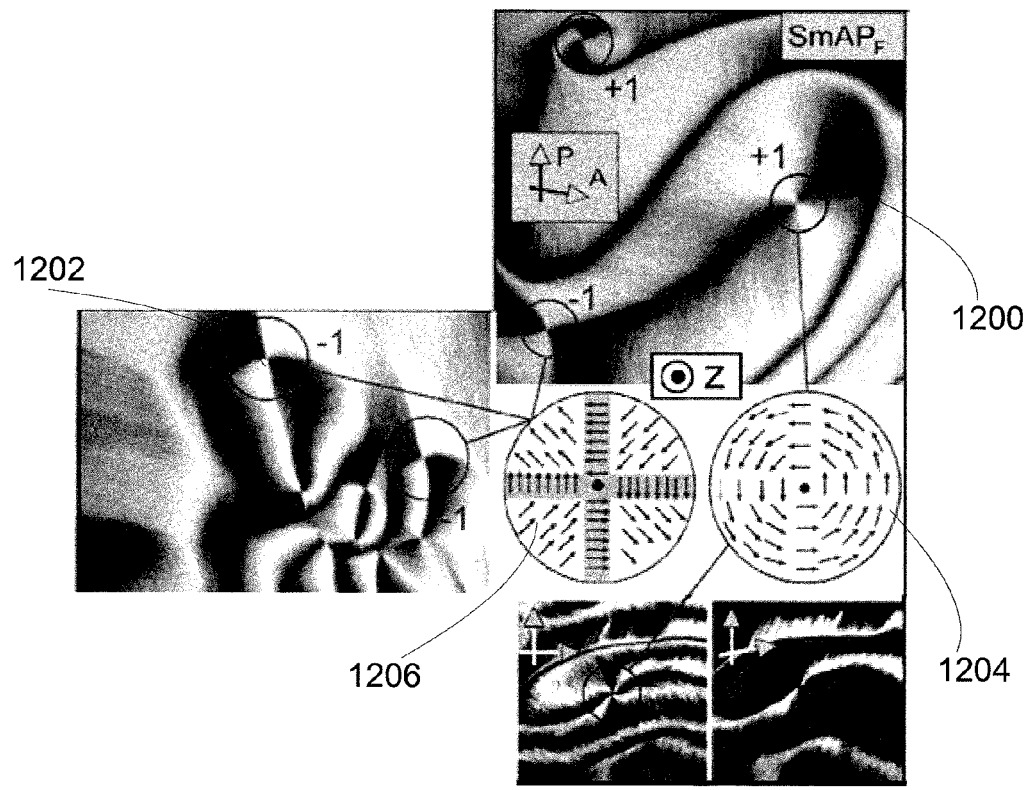
FIG. 12 shows images of freely suspended films with layers parallel to the image plane.

FIG. 12 shows freely suspended films of Compound 2 with layers parallel to the image plane. FIG. 12 show DRLM-film technique images in the $SmAP_F$ phase formed from Compound 2 with oblique incidence (angle of incidence ~7°) and slightly uncrossed polarizers. The images in FIG. 12 reveal a texture of brush patterns, confirming the biaxiality of the $SmAP_F$ phase. In-plane orientational ordering was evidenced by textures of brush patterns 1200 and topological defects 1202 in the in-plane birefringence. Similar in-plane orientation ordering is found in SmC films.

Four-brush pattern 1204, as obtained with crossed polarizer and analyzer, shows topological defects, or vortices, in the textures demonstrating that films have only defect with +2π or −2π reorientation of p. Absence of +π or −π defects indicates that in-plane structure is locally polar, with macroscopic polar order within each layer. 1204 schematically illustrates the +2π (+1) defect, whereas 1206 schematically illustrates the −2π (−1) defect. 1204 and 1206 are distinctly different in that while the local orientation rotates smoothly around the core of +2π (+1) defect 1204, it is broken into four domains of nearly uniform in-plane polarization P=Pp about −2π (−1) defect 1206. This fracturing, to date observed in polar films in which the magnitude of P is at least several hundred nC/cm², is a consequence of the space charge and associated electrostatic energy accompanying splay distortion of P. The about −2π (−1) defect U06 has splay and thus fractures, whereas the +2π (+1) defect U04 can avoid splay of P by adopting a bend-only orientation. Another consequence of the large energy cost of splay of P is the nature of the fluctuations of the film textures.

Figure 13:
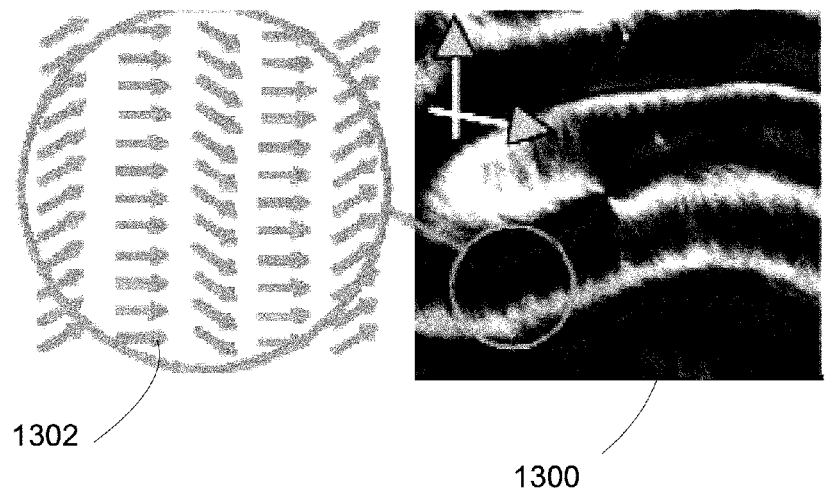
FIG. 13 shows images of a single-layer freely suspended film.

FIG. 13 shows a single-layer (N=1) of freely suspended film formed of Compound 2, exhibiting equal intensity bright brushes emanating from a +2π (+1) defect 1304, as viewed with crossed polarizer and analyzer. Image 1302 indicates that the PA is normal to the film plane. FIG. 13 also shows that space charge suppresses splay fluctuations, leaving predominately bend fluctuations in the sample 1302.

EXAMPLE 3

Electrical and Optical Response of a Tri-Carbosilane Containing Mesogen to Applied Electrical Field The following nonlimiting example teaches by way of illustration, not by limitation, electrical and optical response of a tri-carbosilane modified mesogen, namely Compound 2. In particular, the electrical and optical response of Compound 2 to applied electric field, E, and surface interactions in planar-aligned ITO-on-glass cells was studied vs. T as a probe of the azimuthal orientation and ordering of the molecules about the layer normal, z. Application of a triangle wave voltage v(t) across the cell plates induces peaks in the optical transmission between crossed polarizers and a polarization current (see FIG. 9) in the SmAP$_F$ phase, indicates a Goldstone-like response of macroscopic ferroelectric ordering which we have analyzed in detail.

Assuming that planar alignment so that z is parallel to the glass, giving an index $n_z=\epsilon_z^{1/2}$ for light polarized along z and incident normally on the cell. Taking the azimuthal orientation of the p(Ψ)-z plane to be Ψ, as defined above (FIGS. 5 and 14), the effective index, $n_{eff}$, for light polarized normal to z is given by $1/n_{eff}(Ψ)^2=\sin^2Ψ/n_p^2+\cos^2Ψ/n_o^2$, and the planar cell transmission, for crossed polarizer and analyzer at 45° to z, $T(Ψ)=\sin^2[\pi\, δn(Ψ)d/λ]$, determined by the birefringence $δn(Ψ)=n_z-n_{eff}(Ψ)$, cell thickness d, and wavelength λ. Integration of the current peak (inset of FIG. 14) gives the SmAP$_F$ polarization density $P(T)=P_m<\cos(p_i·p)>$, the first moment of fluctuations of orientations of individual molecular bow planes $p_i$ about the mean orientation p(Ψ), times the molecular polarization density $P_m$. The peaks in the T(Ψ) data were used to extract the dependence of Ψ on applied voltage, Ψ(v), under the assumption that the magnitude of the in-layer plane birefringence $Δn=n_p-n_o$ is independent of Ψ and that Ψ is uniform through the cell thickness. This analysis shows that v(t) α cos Ψ(t) (inset of FIG. 14), just the result first obtained in the "V-shaped" reorientation of P in high polarization chiral SmC materials, shown to be a consequence of the total screening of the applied voltage in the LC by P⊥, the component of P normal to the cell plates, and recently demonstrated in a SmC$_S$P$_F$ bent core phase. In this model, $\epsilon v(t)=2dP\cos Ψ(v(t))$, where $\epsilon$ and d are respectively the dielectric constant and thickness of the insulating alignment layers on the electrode plates. The ~12V width of the 0°<Ψ<180° peaks is consistent with estimates of $\epsilon$ and d and the measured P. These observations provide a self-consistent confirmation of the "block polarization" mode of field-induced reorientation of Ψ, i.e., reorientation with Ψ spatially uniform, and enables the measurement of $n_z-n_o$ (at Ψ=0°) and $n_z-n_p$ (at Ψ=90°), shown in FIG. 14. The polarization magnitude P is determined by integration of the block polarization current peak in FIG. 14. Behavior in the vicinity of the SmA to SmAP$_F$ transition (red crosshatched area, FIG. 14) is difficult to assess because the field required to measure P itself induces a substantial polarization.

Since $\epsilon=n^2$ we have, since Δn is small, $Δn=Δ\epsilon/(2ṅ)=(\epsilon_p-\epsilon_O)/(2ṅ)$, where $Δ\epsilon\, α\, Q(T)=(2<\cos^2(p_i(φ_i)·p)>-1)$, a measure of the second moment of fluctuations of $p_i$ about p. Here the mean in-plane refractive index is given by $ṅ=\sqrt{[(n_p^2+n_o^2)/2]}≈(n_p+n_o)/2$. Data indicate a jump in nz−n and in Q(T) α $n_p-n_o$ through the SmA-SmAP$_F$ transition, with no detectable discontinuity in L(T) at the transition with high XRD resolution (δd=0.02 although L(T) goes through a maximum there. Comparison of the temperature dependence of Δn(T) and P(T) shows that the relationship P(T) α √Δn(T) is rather well satisfied (see squares in FIG. 14).

Figure 15C:
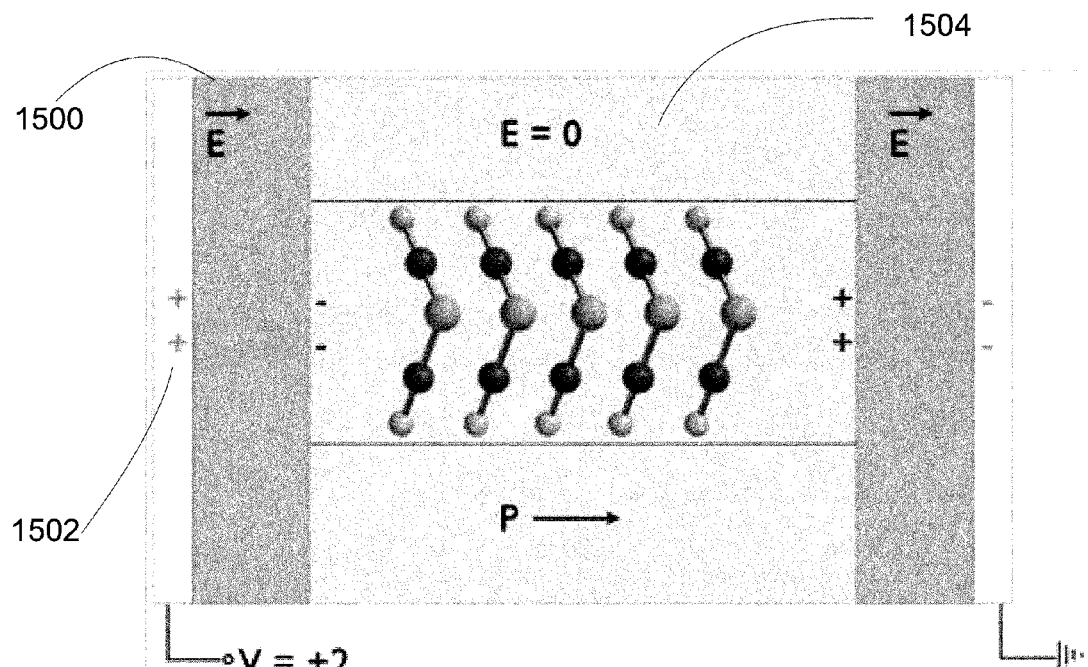
Figure 15D:
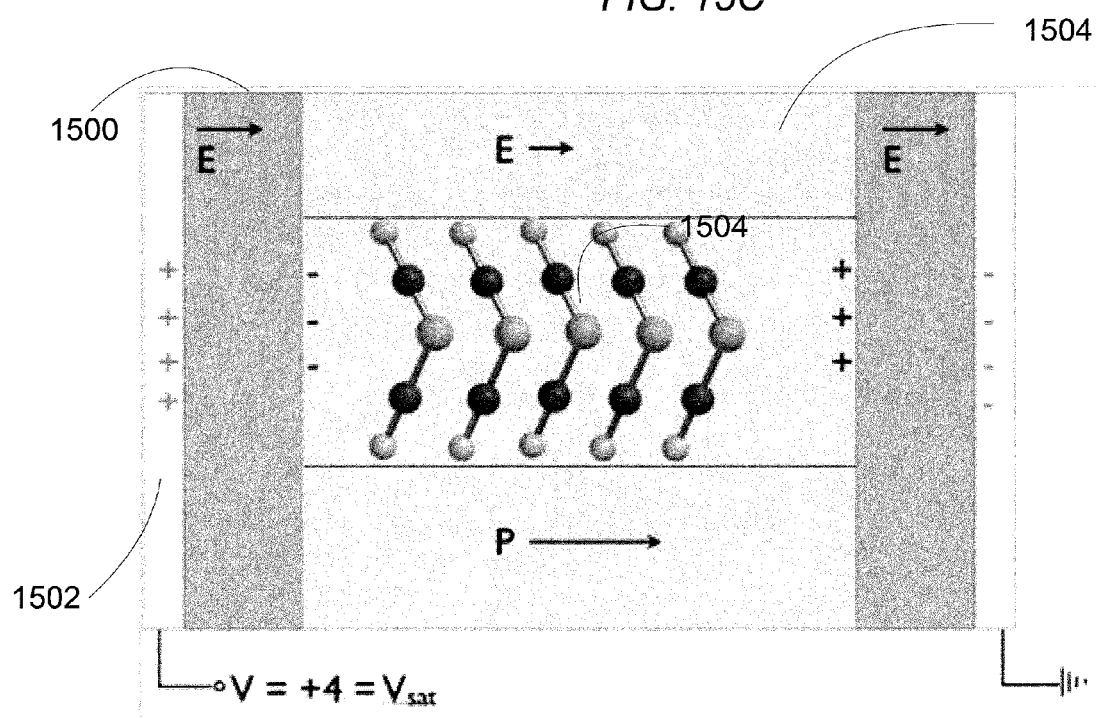
Figure 15E:
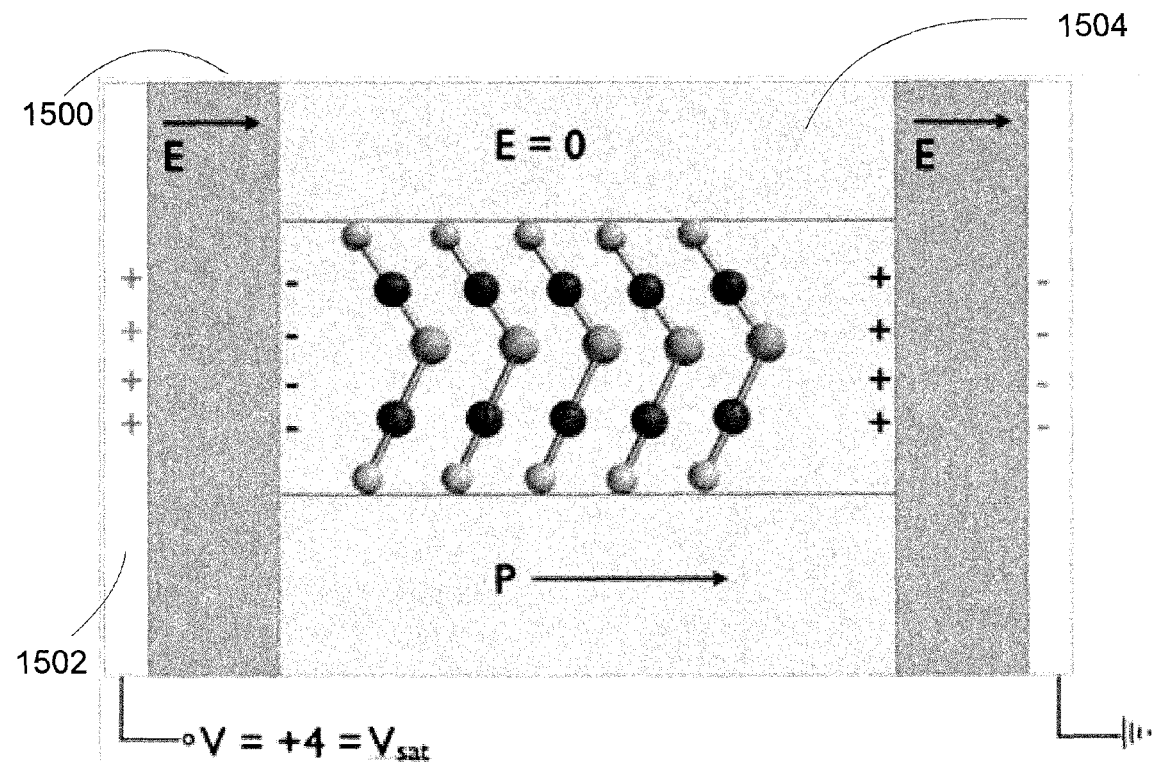

FIG. 15 shows a FLC-based device 1500 containing a conducting material 1502 and liquid crystal material 1504. The device may be operated by control circuitry that drives conducting material 1502 to provide an optically latched state as described below. In the optically latched states, the molecular alignment is preserved by maintaining a constant voltage. By applying additional voltage, the LC material expels additional charges by increasing the molecular bending. Ultimately, a voltage saturation is reached wherein the system achieves a DC balance. Between voltage saturation and zero voltage, the system is undergoing electrostatic V-shape switching without requiring DC balance. By way of example, FIG. 15A shows the FLC-based device without any current, without any applied voltage V, and with no applied electric field E within the LC material. Upon applying voltage to the device (FIG. 15B), an electric field is generated within the LC material with transient power P. FIG. 15C shows the smectic phase material response, effectively neutralizing the applied field in an optically latched state where there is no current, no power consumption, and no net field on the material. that the LC material expels charges through molecular bending to generate an electric field across the alignment layer while concurrently eliminating the electric field within the liquid. FIG. 15D shows a further increase of voltage, again with a transient power response. FIG. 15E shows the further materials response in an optically latched state where there is no current, no power consumption and no net field through the LC material. In one nonlimiting example, conducting material 1502 comprises indium tin oxide (ITO). In one embodiment, the LC material 1504 is about 4.8 μm thick.

Figure 16:
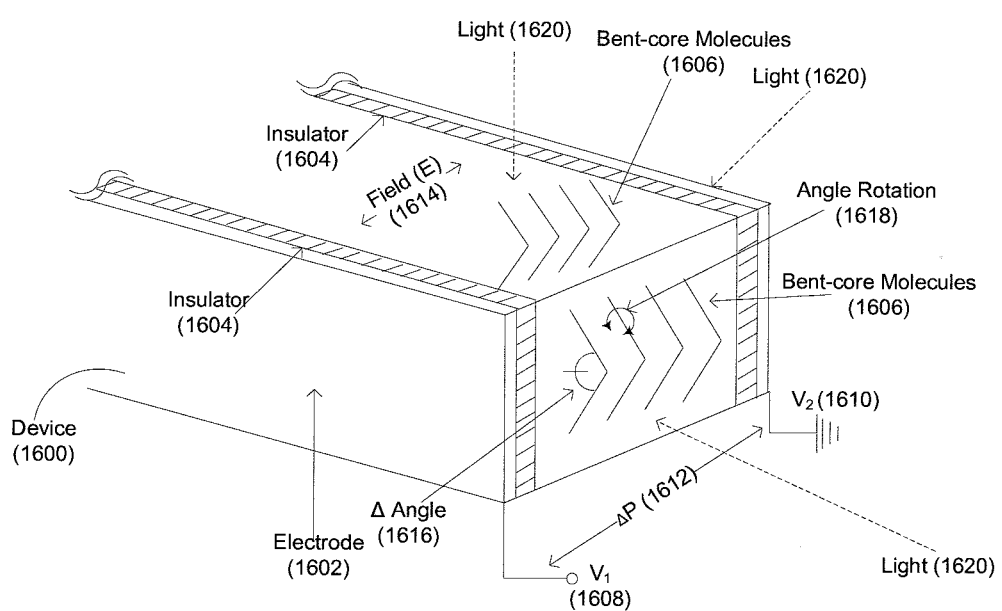
FIG. 16 shows an embodiment of an optical device including FLC materials as described herein.

FIG. 16 shows a FLC-based device 1600 containing an electrode 1602, insulator 1604, and FLC material with bent-core molecules 1606. FIG. 16 shows the FLC-based device with an applied voltage 1608 and ground voltage 1610. Upon application of voltage, the bent-core molecules 1606 decrease angle 1616 and increase polarization 1612. Moreover, with increased voltage, the bent-core molecules vary angle rotation 1618. Light 1620 may enter device 1600 from x, y, and z directions or combinations thereof. In one embodiment, the insulator 1604 comprises polyimide.

Figure 17:
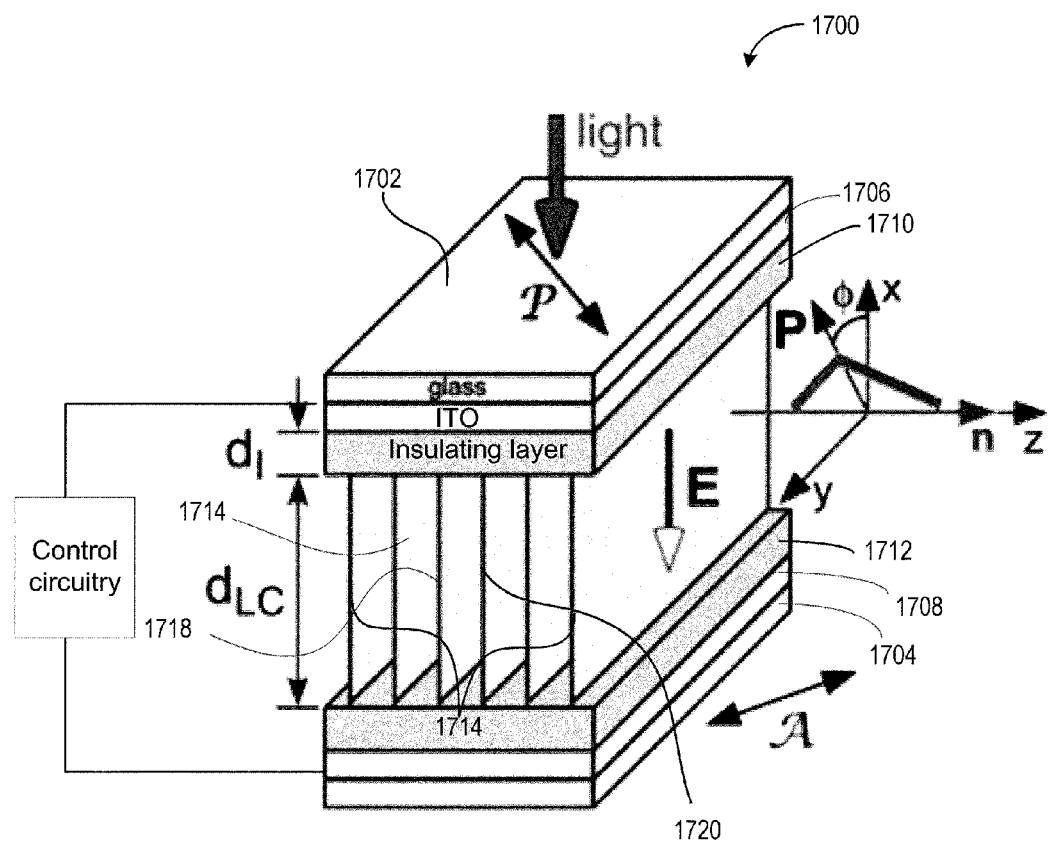
FIG. 17 shows one embodiment of an optical device including FLC materials as described herein.

FIG. 17 shows an alternative embodiment as device 1700. Opposed planes of transparent insulating material, such as glass 1702, 1704, enclose conducting layers 1706, 1708, which may be, for example, indium tin oxide. Dielectric or insulating layers 1710, 1712 are next in sequence leading to an interior 1714 of ferroelectric smectic liquid crystal material as described above, all of this forming a light transmissive pathway 1715. The interior 1714 contains mesogens as shown in FIGS. 2-14 that self assemble under the influence of field E to present their respective elongate axes in parallel with respect to direction z. The tails of the mesogens interdigitate to form respective layers 1716, 1718, 1720.

Figure 18:
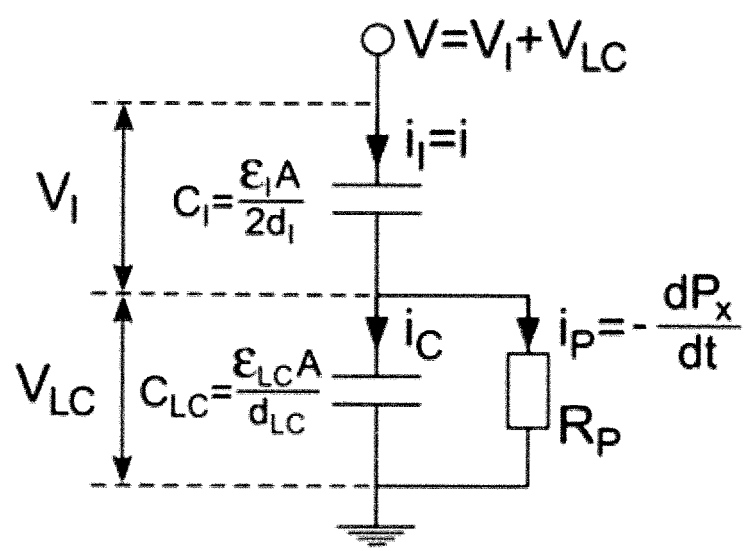
FIG. 18 is an electrical schematic of the circuit formed by the embodiment of FIG. 17.
Figure 19:
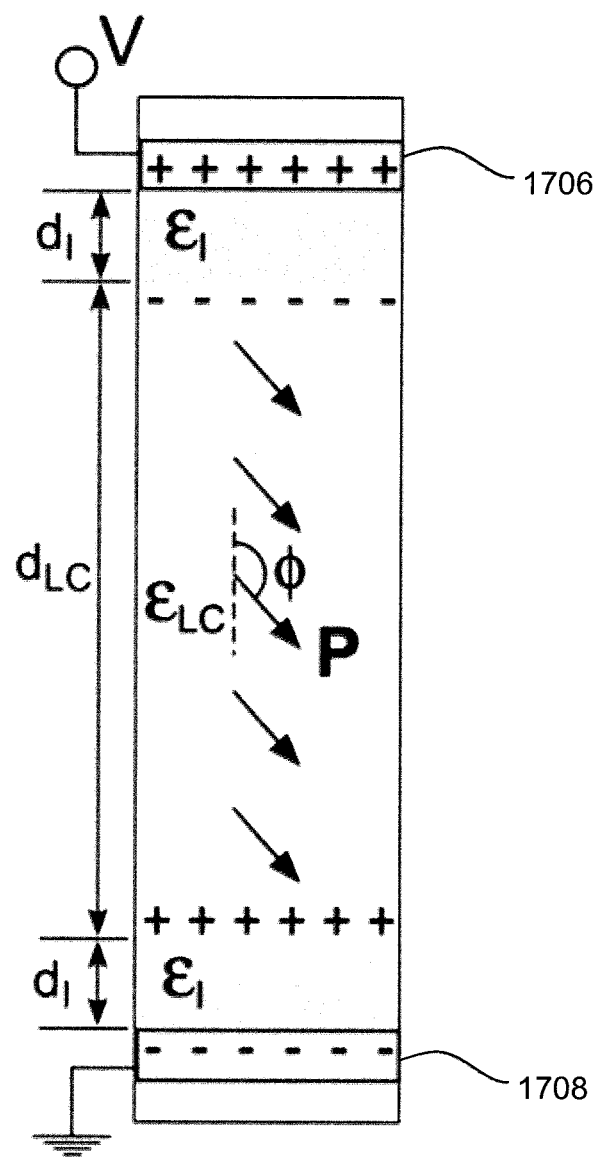
FIG. 19 shows reorientation of a polarization angle in the FLC material that is brought about by operation of circuitry as shown in FIG. 18.

Control circuitry 1718 switches the interior 1714 between optically transmissive and optically opaque states by the application of control voltage V as shown in FIG. 18. The voltage V controls the optical state of the mesogens in interior 1714 by varying the polarization angle $\Phi$ of the mesogens. The angle $\Phi$ varies transiently as a function of field E between the conductors 1706, 1708, as a function of the applied voltage $V_{LC}$. During this transient state, the control circuitry must also contend with the parasitic capacitance $C_1$ of insulating layers 1706, 1708 shown in FIG. 18 as $V_1$. The mesogen response consumes power by the action of current $i_p$. Voltage clamping then provides for optical latching after the mesogens have fully responded to the applied field, thus cancelling the effect of field E upon conductor 1708. As shown in FIG. 19, these operations change the optical state of the interior 1714 by adjusting the polarization angle $\Phi$ of the mesogens forming the interior 1714. Thus, the mesogens of interior 1714 may be switched from a substantially opaque optical state to an optically transmissive state, as well as one or more grey-scale states therebetween with optical latching at each state, all by the application of different voltages V.

Figure 20:
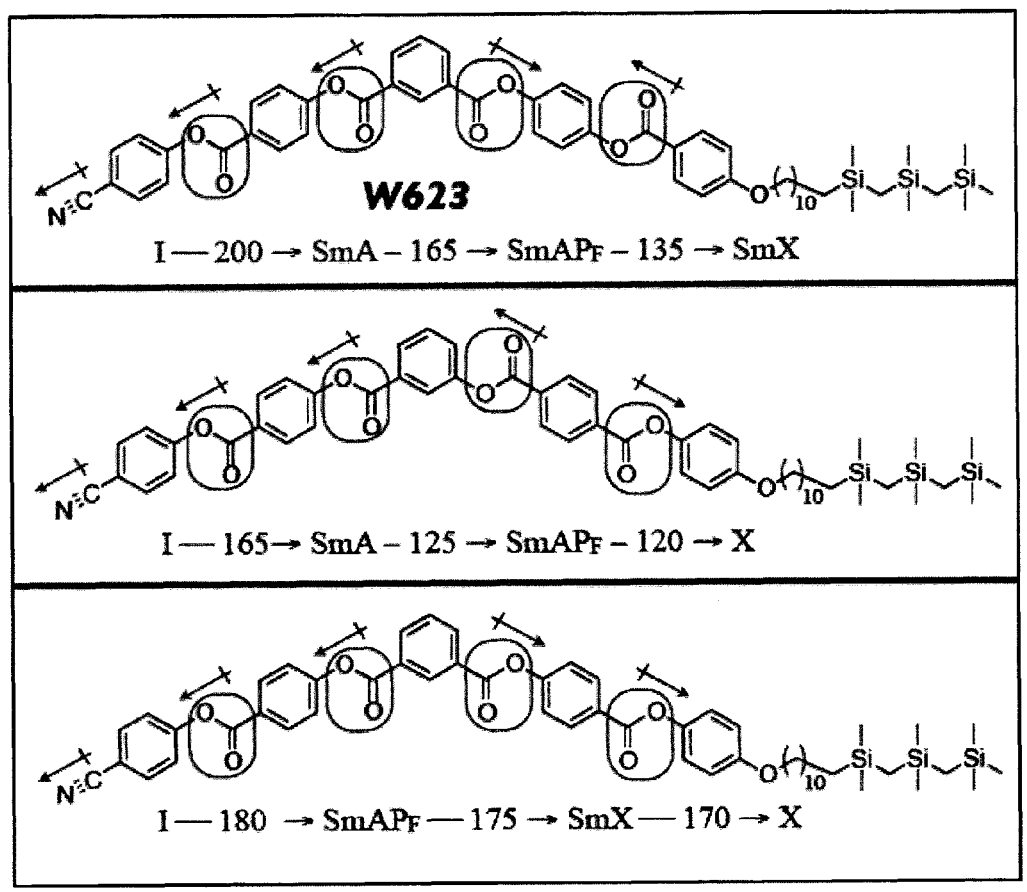
FIG. 20 shows that different isomers of Compound 2 (see FIG. 2) demonstrate ferroelectric phase behavior at different temperatures.
Figure 21:
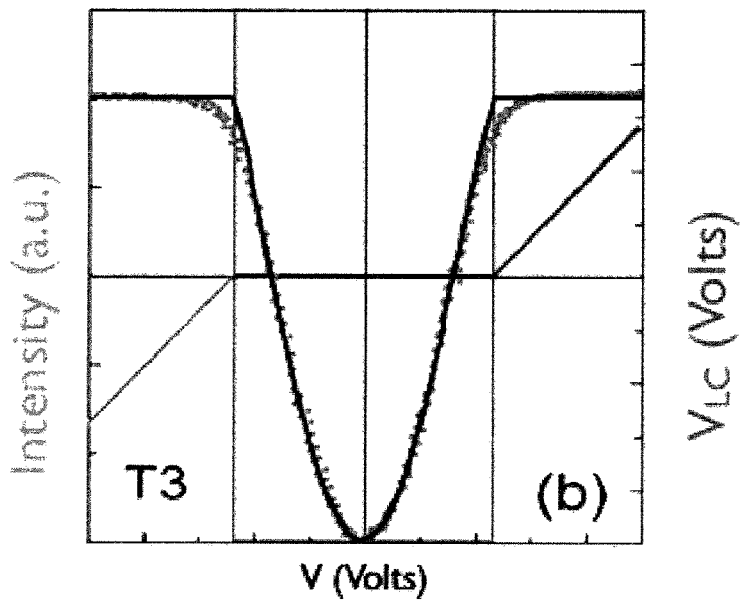
FIG. 21 shows that Compound 2 has nearly perfect ferroelectric switching behavior.
Figure 22:
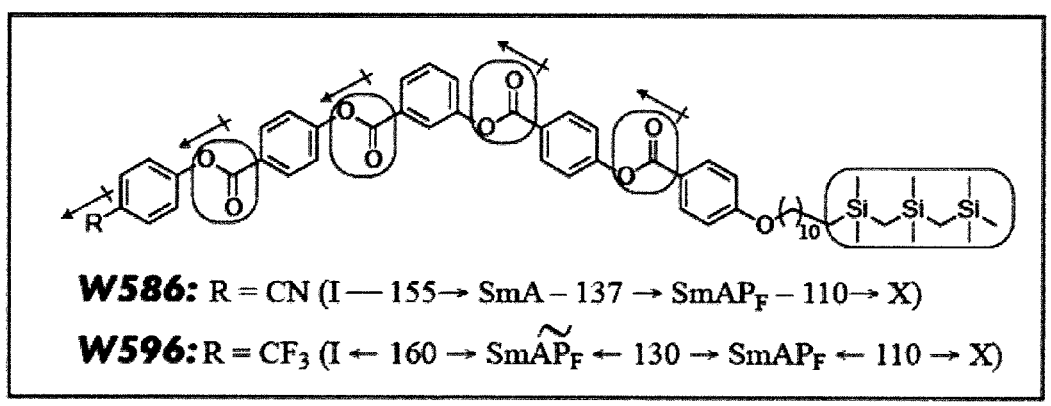
FIG. 22 shows the temperature ranges for alternative embodiments of FLC molecules according to the present disclosure.

FIG. 20 shows that various isomers of Compound 2 (here named also W623) all achieve the ferroelectric phase $AmAP_F$, but they do so at different temperatures, i.e., 135° C. to 165° C. for isomer (a), 120° C. to 125° C. for isomer (b), and 170° C. to 175° C. for isomer (c). FIG. 21 shows ferroelectric switching of Compound 2 that closely approximates the theoretical ideal.

FIG. 21 shows other compounds designated W586 and W596. These achieve the ferroelectric phase $SmAP_F$, respectively, at temperatures 110° C. to 137° C. and 110° C. to 130°.

Those of ordinary skill in the art will appreciate that insubstantial changes may be made in the above methods and systems without departing from the scope hereof. It should be noted that the matter contained in the above description or shown in the accompanying drawings should be interpreted as illustrative and not in a limiting sense. The following claims are intended to cover all generic and specific features described herein, as well as all statements of the scope of the present method and system and reasonable variations thereof, which, as a matter of language, might be said to fall therebetween.

What is claimed is:

1. A material formed of molecules capable of demonstrating ferroelectric phase behavior in liquid crystal form, comprising molecules of the formula:

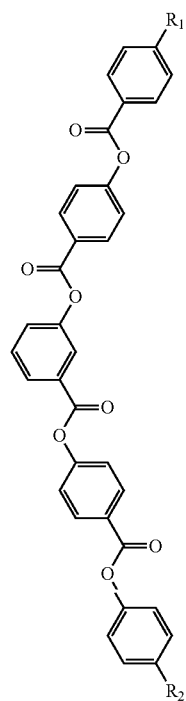

wherein $R_1$ is selected from the group consisting of O—$R_{1a}$—$R_{1b}$ wherein
$R_{1a}$ is $(CH_2)_n$ with n being an integer from 1 to 15;
$R_{1b}$ is $(Si(R_1)_2)_q$—$Si(R_1)_3$ where $R_1$ is alkyl, and q is an integer from zero to three; and
$R_2$ is selected from the group consisting of C≡N, $NO_2$; O—$CF_3$, and $C_4F_9O$—$C_2F_4O$—$CF_2CH_2O$.

2. The material of claim 1, wherein
n is an odd integer, and
$R_{1b}$ is selected from the group consisting of $Si(CH_3)_2Si(CH_3)_2Si(CH_3)_3$; $Si(CH_3)_2Si(CH_3)_3$; $Si(CH_3)$; $Si(C_2H_5)_2Si(C_2H_5)_3$; and $Si(C_2H_5)_3$.

3. The material of claim 2 wherein $R_2$ is C≡N.

4. The material of claim 3 wherein $R_1$ is $Si(CH_3)_2Si(CH_3)_2Si(CH_3)_3$.

5. In a liquid crystal electro-optic device, the improvement comprising the material of any one of claims 1-4 forming the interior of a liquid crystal display.

6. The device of claim 5, further comprising the control circuitry operable to change the optical state from a substantially opaque state to an optically transmissive state.

7. The liquid crystal electro-optic device of claim 6, including control circuitry operable to change the optical state of the material from a substantially opaque state to an optically transmissive state, as well as one or more grey scale states in-between the optically transmissive state and the substantially opaque state.

8. A method for operating a liquid crystal electro-optic device, comprising:
providing a material according to claim 1 between two electrodes;
permitting the material to assemble into a plurality of layers;
applying a first switching voltage to the electrodes to facilitate switching of the material; and
maintaining a constant voltage on the electrodes to facilitate optical latching that maintains the material in a first optical state.

9. The method of claim 8, wherein the step of applying voltage is performed without regard to any requirement for imposing DC balance upon the material.

10. The method of claim 8, further comprising a step of, thereafter, applying a second switching voltage to the electrodes so as to achieve a second optical state and maintaining another constant voltage on the electrodes that maintains the material in a second optical state.

11. The method of claim 10, wherein at least one of the first switching voltage and second switching voltages is zero volts.

* * * * *